US00PP10675P

United States Patent [19]

Lyrene

[11] Patent Number: Plant 10,675

[45] Date of Patent: Nov. 10, 1998

[54] LOW-CHILL HIGHBUSH BLUEBERRY "STAR"

[76] Inventor: Paul Lyrene, 1143 Fifield Hall Horticultural Sciences Dept., Univ. of FL, Gainesville, Fla. 32611

[21] Appl. No.: 523,357

[22] Filed: Sep. 5, 1995

[51] Int. Cl.[6] ..... A01H 5/00

[52] U.S. Cl. ..... Plt./33.1

[58] Field of Search ..... Plt./33.1

[56] References Cited

PUBLICATIONS

Galleta, Gene J., "Blueberries and Cranberries" *Advances in Fruit Breeding* 1975 Purdue Research Foundation, West Lafayette, Ind. pp. 154–185.

*Primary Examiner*—James R. Feyrer

[57] ABSTRACT

A new and distinct low-chill highbush blueberry variety. Its novelty consists of the following unique combination of features:

1. The ability to flower and leaf vigorously in an area where the mean temperature of the coldest month is 58 degrees F.
2. The ability to produce ripe fruit 60 days after flowering in north-central Florida
3. The ability to ripen 80% of its crop between April 20 and May 10 in north-central Florida.
4. Produces fruit that are large and firm with good flavor and firmness and a small pedicel scar.
5. Produces a plant with tolerance to *Phytophthora cinnamomi* and *Botryosphaeria dothidia*.
6. Can readily be propagated from softwood cuttings.

3 Drawing Sheets

BACKGROUND OF THE INVENTION

The blueberry plant of this disclosure is mainly *Vaccinium corymbosum,* although other Vaccinium species, principally *Vaccinium darrowi* occur in the ancestry as a source of low chilling requirement genes. This plant was the product of a planned breeding program which was conducted to develop new varieties of blueberries which were adapted for culture and production in the warmer areas within the Sunbelt states, and in areas of local markets where blueberries have not traditionally been produced on a large scale. Low-chill varieties of blueberries would offer a new money crop to southern growers and thereby enhance diversity in the selection of high value commodities available to growers with enterprises of different scales. Blueberry varieties which bear fruit ahead of that produced in the more traditional, northern production areas could capture premium early market prices in this expanding commodity; and, would present an attractive option for large scale producers and "pick-your-own" enterprises, and could enhance the selection of fruit-bearing plants available to home gardeners. Having the option of blueberry production could make better use of available labor resources in seasons of low activity which could otherwise cause labor crews to move on to other production areas while not competing with requirements of other major commodities. It is an object of the subject planned breeding program to develop varieties of blueberries which are adapted for production of high quality fruit in sufficient quantities to allow for the profitable production of this commodity in warmer areas of the southeastern United States on a commercial scale, yet still be adapted for culture on a small scale such as in the home garden. The subject of this disclosure is such a variety resulting from the planned breeding program.

'Star' originated as a seedling selected from the cross FL80-31×O'Neal. The seed that gave rise to 'Star' was produced by hand-pollination in a greenhouse in Gainesville, Fla. in 1981. 'O'Neal' is an unpatented cultivar introduced in 1987 by North Carolina State University. FL80-31 is an advanced selection from the Florida breeding program that was selected in 1980. 'Star' was selected in a high-density fruiting nursery in Gainesville, Fla. in 1983, and was first propagated for further testing in 1987 under the number FL87-139-S. Replicated test plots in Gainesville and at several other points in north Florida and south Georgia were observed between 1989 and 1995, during which time the desirable features of this clone became apparent.

'Star' is tetraploid, with 48 somatic chromosomes, which is typical of highbush blueberry. Although the plant is partially self-compatible and will produce some fruit after self-pollination, the fruit will be earlier-ripening, larger, and more abundant if 'Star' is cross-pollinated by another highbush blueberry cultivar.

SUMMARY OF THE INVENTION

'Star' differs from other southern highbush cultivars in that it combines very low chill requirement, early fruit ripening, high fruit quality, and a very short harvest period. In contrast to most southern highbush cultivars, 'Star' has a chilling requirement low enough to allow it to be grown as far south as Gainesville, Fla., with no delay in spring budbreak. In Gainesville, the mean January temperature is 56° F, with an average of about 400 hours per winter with temperatures below 45° F. 'Star' flowers early; the mean date of 50% anthesis in Gainesville is February 25. 'Star' ripens very early. The mean date of mid-harvest averages May 1 at Gainesville. This is 10 to 14 days earlier than the mean ripening date for 'Southmoon'. Compared to 'Sharpblue', the most widely-planted Florida highbush blueberry cultivar, 'Star' ripens all of its fruit in 3 weeks compared to 8 weeks for 'Sharpblue'. This is an advantage in that a short harvest period reduces harvest costs and concentrates most of the harvest at a time of the year when market prices are highest. 'Star' avoids the excessive fruit-bud set and poor spring leafing that is problematic with the cultivar 'Misty'. 'Star' has excellent picking scar and fruit firmness, which avoids the serious post-harvest problems presented by the cultivar 'Gulf Coast'. The fruit of 'Star' are medium to large, averaging about 1.6 grams per berry. Berries are dark blue in color. The small, dry pedicel scar and high firmness give the berries a long post-harvest life. Both flavor and texture are excellent. The plant can be propagated easily from softwood cuttings. It has been propagated by this method on numerous occasions, and without exception, the resulting plants have displayed the varietal characteristics. The open fruiting cluster, the high berry firmness, the excellent scar, and the synchronous ripening make mechanical harvest of 'Star' berries possible, although the berries are normally harvested by hand when market prices are high.

BOTANICAL DESCRIPTION OF THE CLAIMED PLANT

Figure 1:
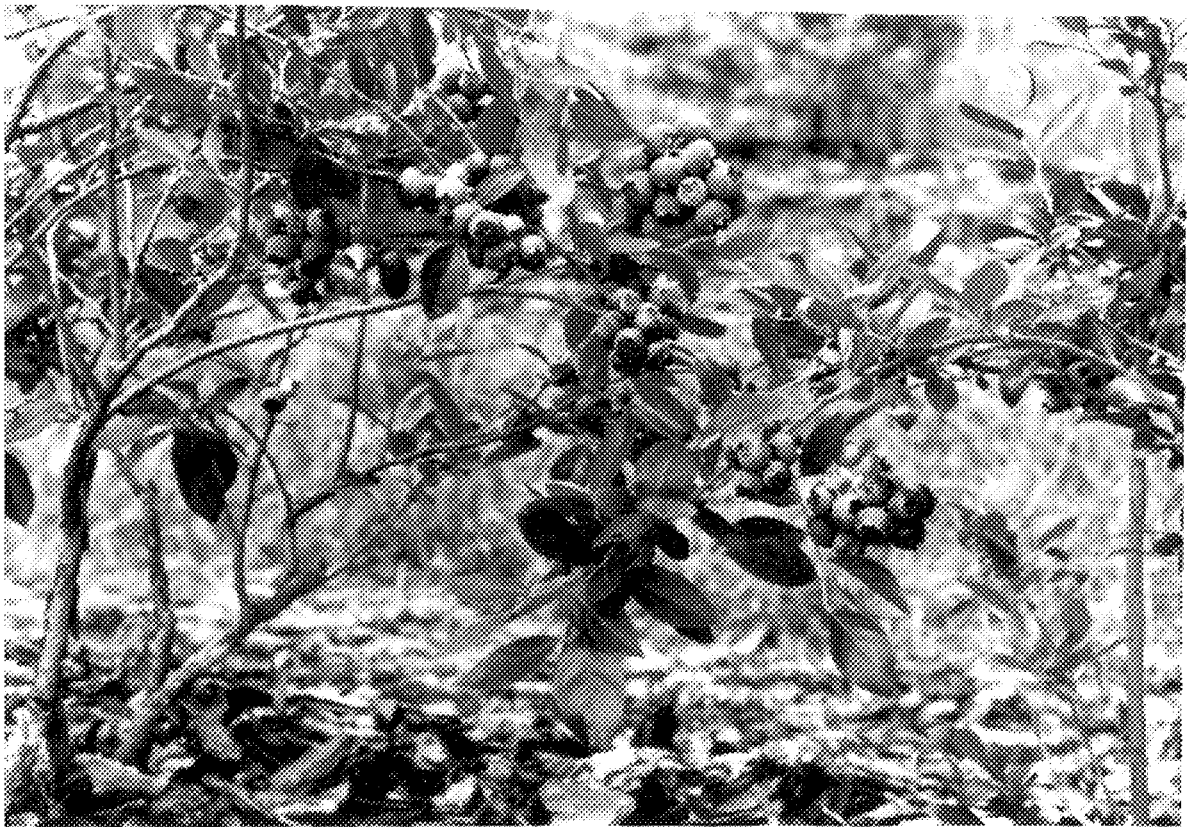
FIG. 1 illustrates portions of 3-year-old specimens of the plant 'Star' in side elevation and shows the multiple trunk, branch scaffolding, and pose of the branches. All stages of bark maturity are depicted in this figure. The FIG. 1 photograph also depicts the canopy and fruit clusters of the plant at a seasonal stage approaching the harvest period in early May in Central Florida, and both upper and lower leaf surfaces.
Figure 2:
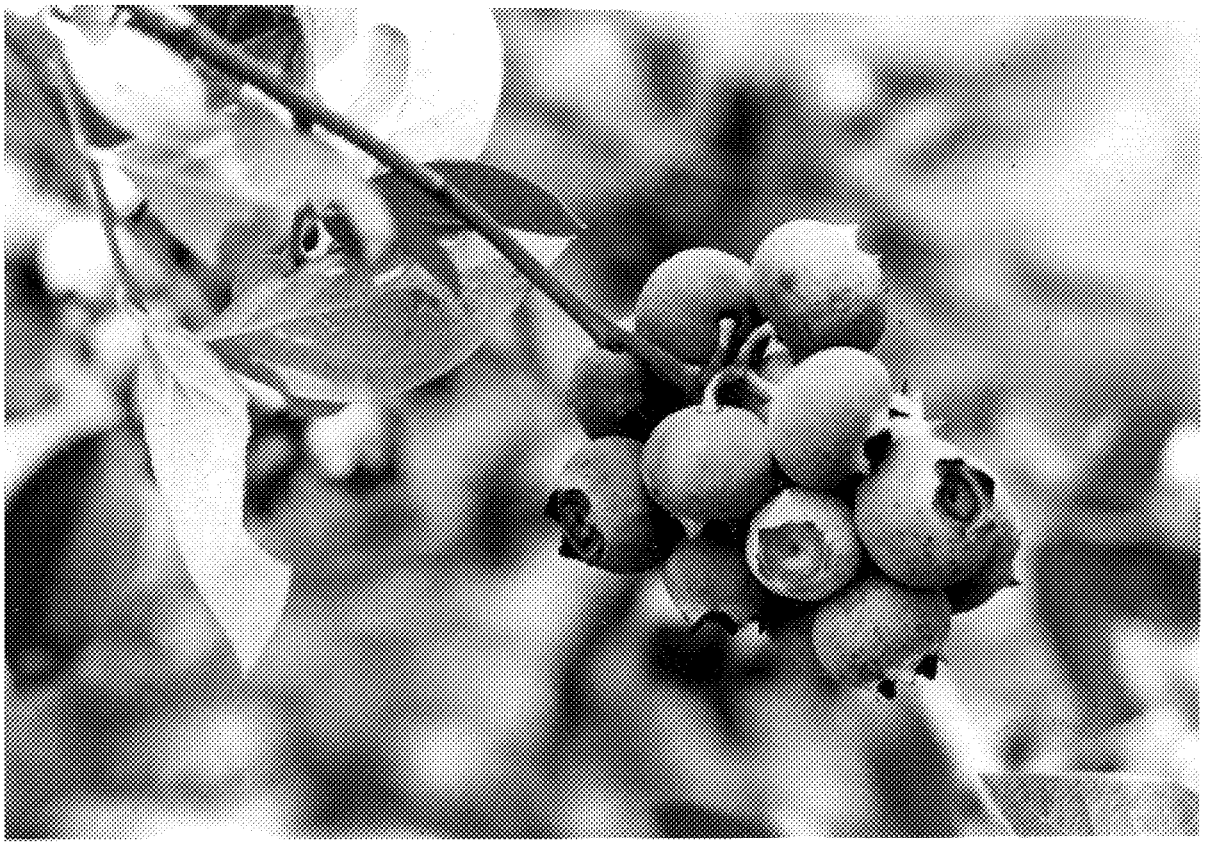
FIG. 2 shows, at close range, the blossom end of the fruit with the crown-shaped calyx and pointed protrusions. This photograph reflects the coloration of fruit in the ready to pick stage, the surface bloom coloration of the berries, the pedicel of the fruit, and the bottom surfaces of several leaves.
Figure 3:
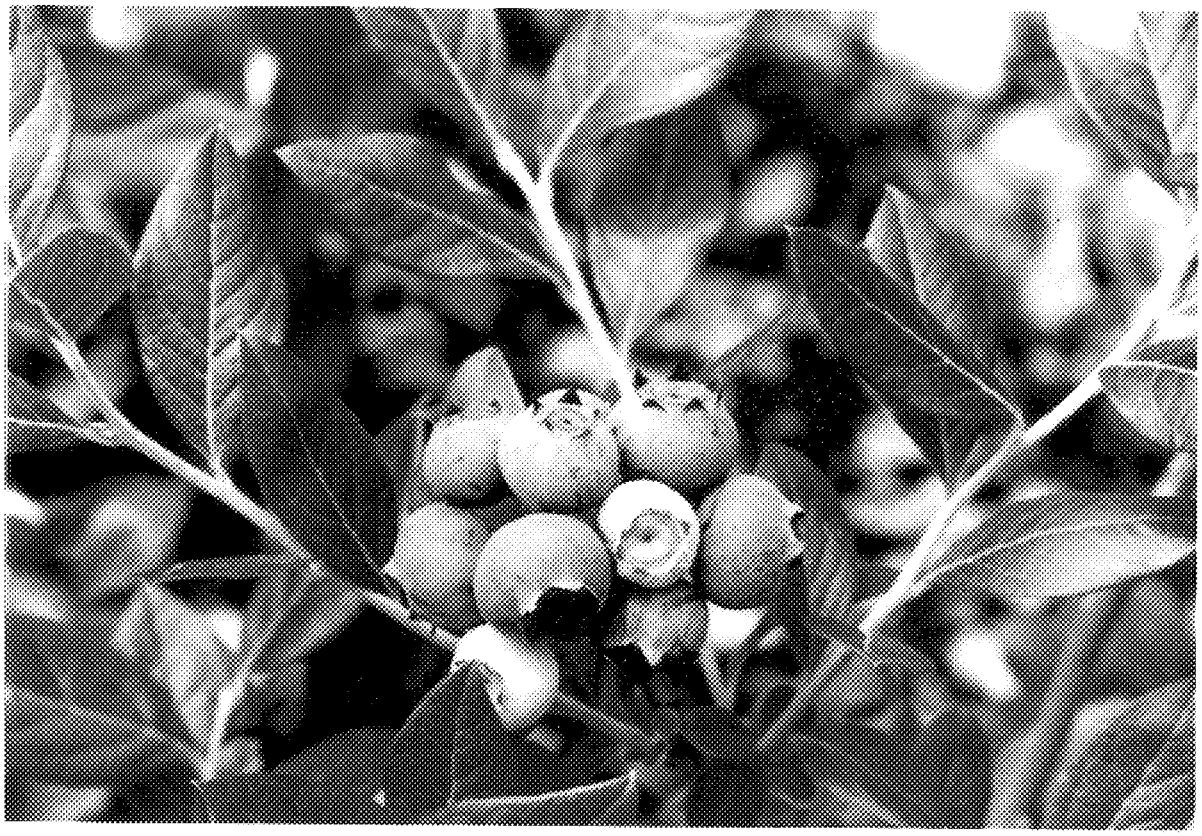
FIG. 3 depicts a further fruit cluster typical of the plant of this disclosure with the exceptionally attractive fruit, the outstanding close range of maturity of fruit and the upper surfaces of leaves of the described plant.

'Star' is a hybrid based on *Vaccinium corymbosum.* It is called a "southern highbush" variety because it has a low chilling requirement which was bred using genes from the native wild Florida blueberry species, *Vaccinium darrowi.* 'Star' originated from the cross FL80-31×O'Neal.

The following is a detailed botanical description of 'Star' based on observation of specimens grown in Gainesville, Fla. Color descriptions, except those given in common terms, use terminology from "The Pantone Book of Color", 1990, by Leatrice Eiseman and Lawrence Herbert. Harry N. Abrams, Inc. Publishers, New York.

Bush:

*Size.*—Medium. Rooted cuttings after 2 years in the field about 140 cm tall with diameter of spread about 90 cm.

*Growth habit.*—Moderately upright.

*Productivity.*—Moderate. Three-year-old plants yield 1 to 2 kg per plant.

*Flower bud number.*—Below average numbers for southern highbush. This reduces overfruiting problems.

*Disease resistance.*—Medium resistance to Phytophthora root rot and Botryosphaeria stem blight.

*Range of adaptation.*—In Florida, north of Ocala, and in southeast Georgia. May be productive in other states along the Gulf and South Atlantic coasts to southeastern North Carolina on sites where spring freezes are infrequent and soils are favorable.

Trunk:

*Suckering tendency.*—Tendency to sprout new shoots from rhizomes is intermediate compared to the norm for southern highbush cultivars. Sufficient numbers of new canes are produced to renew the bush but not so many as to elevate the cost of pruning the plant. Annual pruning is normally done on 'Star' in Florida to invigorate the bush. This may involve both post-harvest summer "topping" and the removal of old canes at the base in winter.

*Bark texture.*—Bark on older trunks rough but exfoliates to smooth.

*Color.*—Two-year-old wood slate green (Pantone 16-0713).

Twigs:

*Color.*—Current-season twigs in August are golden-green (Pantone 15-0636).

*Internode length.*—on strong, upright shoots averages 1.5 cm.

Leaves:

*Size.*—Medium, average length 50 mm; average width 25 mm.

*Leaf margin.*—entire.

*Color of upper leaf surface.*—Avocado (Pantone 18-0430).

*Color of lower leaf surface.*—Moss tone (Pantone 17-0525).

*Pubescence on upper leaf surface.*—Glabrous, except numerous short, white hairs on midrib visible at 30×.

*Pubescence on lower leaf surface.*—A few stalked glands on midrib visible at 30X. Otherwise glabrous.

*Pubescence on leaf margins.*—Very small glands spaced along the margins of the petiolar half of the blade.

Flowers:

*Size.*—Medium. Flower averages 12 mm long from point of pedicel attachment to the tip of the corolla. The corolla tube at the widest part averages 10 mm across.

*Color.*—White.

*Shape.*—Urceolate.

*Pollen production.*—Copious.

*Flowering period.*—Early; 50% anthesis averages February 25 in Gainesville, Fla.

*Self-fruitfulness.*—Partially self fruitful but produces more fruit and larger fruit if cross-pollinated by another highbush blueberry cultivar.

Berry:

*Size.*—Large, about 1.6 grams per berry. About 14 mm high and 18 mm wide.

*Color.*—Cadet. Pantone 18-3812.

*Pedicel scar.*—Small and dry.

*Firmness.*—Very firm.

*Calyx lobes.*—Well-developed, crown-shaped.

*Texture.*—Good. Small seeds, thin skin, few sciereids.

*Surface wax.*—Moderately persistent.

*Maturity date.*—Early; averages May 1 for mid-harvest at Gainesville.

I claim:

1. A new and distinct highbush blueberry plant, substantially as illustrated and described, characterized by its low chilling requirement, large fruit, high fruit quality, early ripening, and resistance to Phytophthora root rot and Botryosphaeria stem blight, having the ability to be asexually propagated by softwood cuttings.

* * * * *